US00PP35603P3

(12) United States Plant Patent
Fouillet

(10) Patent No.: US PP35,603 P3
(45) Date of Patent: Jan. 30, 2024

(54) APPLE TREE NAMED 'R205'

(50) Latin Name: ***Malus domestic* Borkh.**
Varietal Denomination: R205

(71) Applicant: IFO S.A.R.L., Seiches-sur-le-Loir (FR)

(72) Inventor: Valérie Fouillet, Saint Sylvain d'Anjou (FR)

(73) Assignee: IFO S.A.R.L., Seiches sur le Loir (FR)

( * ) Notice: Subject to any disclaimer, the term of this patent is extended or adjusted under 35 U.S.C. 154(b) by 4 days.

(21) Appl. No.: 18/122,671

(22) Filed: Mar. 16, 2023

(65) Prior Publication Data

US 2023/0320242 P1 Oct. 5, 2023

(30) Foreign Application Priority Data

Apr. 4, 2022 (FR) ..... 21286

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 5/0875
See application file for complete search history.

*Primary Examiner* — Kent L Bell
(74) *Attorney, Agent, or Firm* — Michelle Bos Legal LLC

(57) ABSTRACT

'R205' is a new apple tree notable for its fruit, which exhibits attractive dark red skin and red and white flesh and is well-suited for the fresh market.

6 Drawing Sheets

Latin name: *Malus domestica* Borkh.
Variety denomination: 'R205'.

BACKGROUND OF THE VARIETY:

'R205' is a new and distinct variety of apple tree (*Malus domestica* Borkh.) obtained from a controlled cross of 'S.157' (female parent, not patented) x 'HY63-2' (male parent, not patented) carried out at Seiches-sur-le-Loir, France in 2007. Seeds obtained from the cross were planted at Seiches-sur-le-Loir, and 'R205' (originally identified by breeder's reference 'CR71-4') was selected from the resulting seedlings for propagation and further observation. 'R205' was first asexually propagated by grafting at Seiches-sur-le-Loir in 2014, and has since been observed to remain true to type through successive asexually propagated generations.

BRIEF DESCRIPTION OF THE VARIETY

The 'R205' apple tree is distinguished by its fruit, which exhibits attractive dark red (greyed-purple 187A) skin and red and white flesh and is well-suited for fresh consumption. Comparisons of 'R205' to its parents and to similar variety 'R201' (U.S. Plant Pat. No. 28,218) are shown in Tables 1, 2 and 3 below.

TABLE 1

Comparison of 'R205' to Female Parent 'S.I57'

| Characteristic | 'R205' | 'S.I57' |
|---|---|---|
| Flesh color | Red N45C on 80%; White N155C on 20% | Yellow-white 158A |
| Amount of over color on fruit skin | 99% | 85% to 95% |

TABLE 1-continued

Comparison of 'R205' to Female Parent 'S.I57'

| Characteristic | 'R205' | 'S.I57' |
|---|---|---|
| Fruit shape | Cylindrical | Conic |
| Attitude of leaves in relation to shoot | Upwards | Outwards |
| Color of petal upper surface | Red-purple 71B | White-pink 69D |

TABLE 2

Comparison of 'R205' to Male Parent 'HY63-2'

| Characteristic | 'R205' | 'HY63-2' |
|---|---|---|
| Eating quality | Good | Not edible |
| Storageability | Medium | Weak |
| Fruit shape | Cylindrical | Conic |
| Flesh texture | Medium to coarse | Very coarse |
| Acidity at harvest time | Medium | High |

TABLE 3

Comparison of 'R205' to Similar Variety 'R201'

| Characteristic | 'R205' | 'R201' |
|---|---|---|
| Diameter of fully open flower | 29 mm | 50 mm |
| Brix | 12 | 15 |
| Amount of russet around stalk cavity | Weak to medium | Large |
| Bark color | Greyed-purple N187D and Greyed-orange 166A | Grey N200C |
| Leaf blade margin | Serrulate | Biserrate |

BRIEF DESCRIPTION OF THE PHOTOGRAPHS

The accompanying photographs were obtained in 2020 and 2021 at Seiches-sur-le-Loir, France. The bare branches, blossoms and leaves shown are on trees planted in 2015; the fruits shown were grown on trees planted in 2020.

DETAILED BOTANICAL DESCRIPTION OF THE VARIETY

Figure 1:
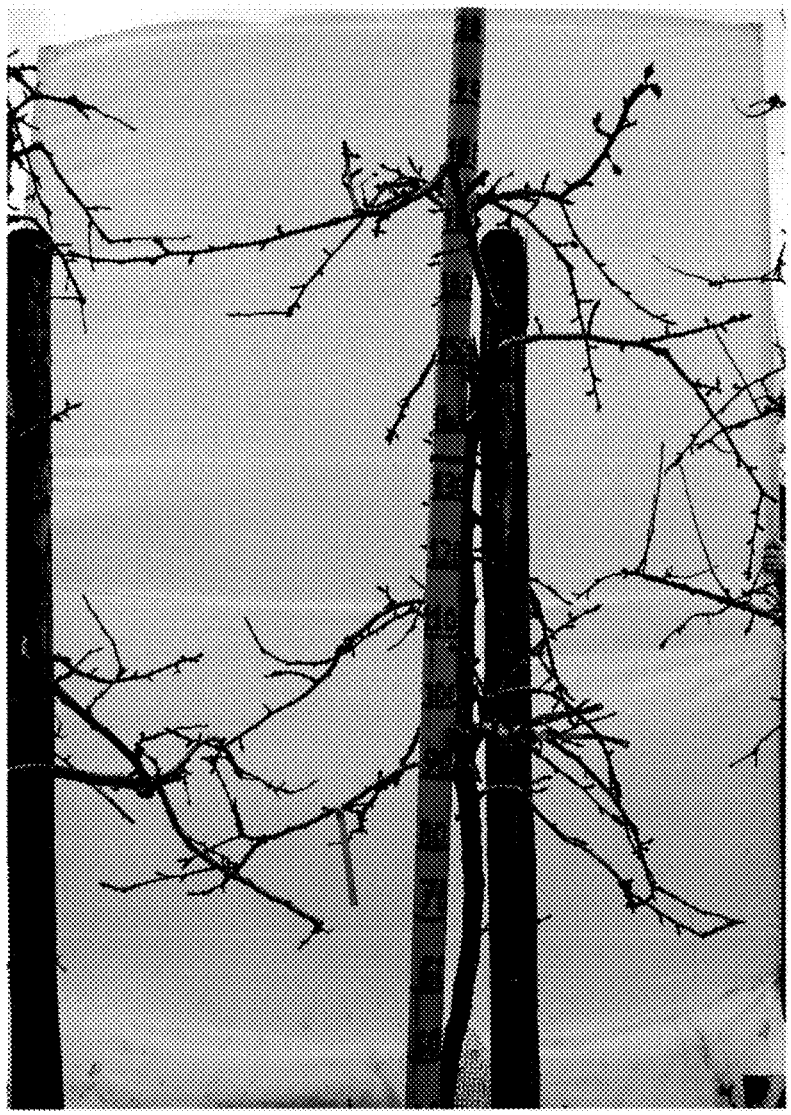
FIG. 1 is a photograph of an 'R205' apple tree.
Figure 2:
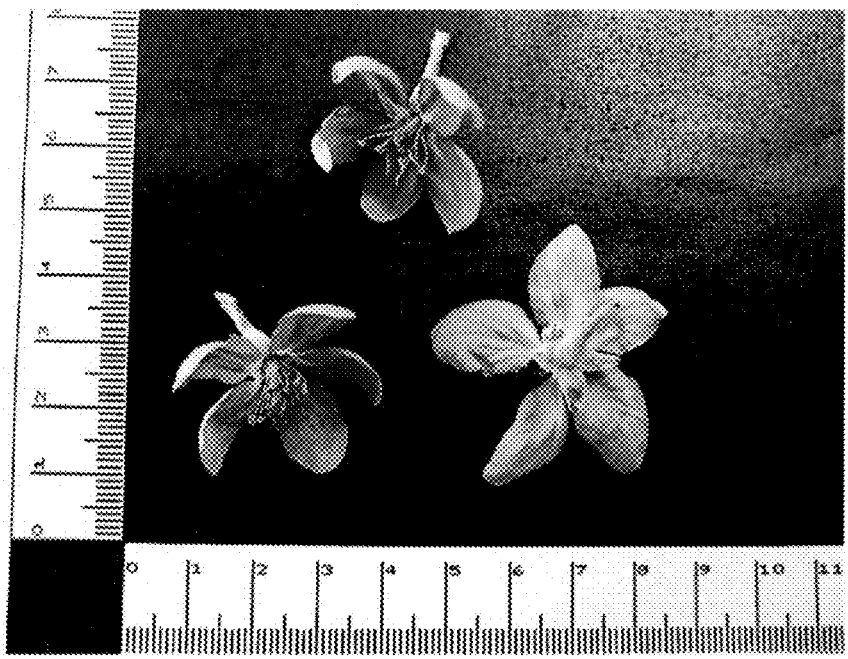
FIG. 2 is a photograph of blossoms from an 'R205' apple tree.
Figure 3:
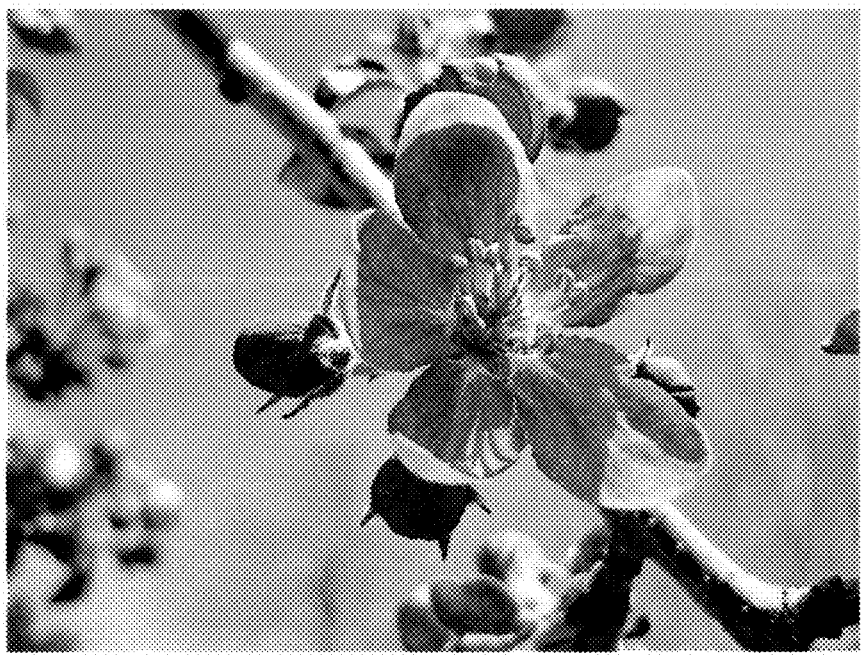
FIG. 3 is a photograph of a blossom and flower buds on an 'R205' apple tree.
Figure 4:
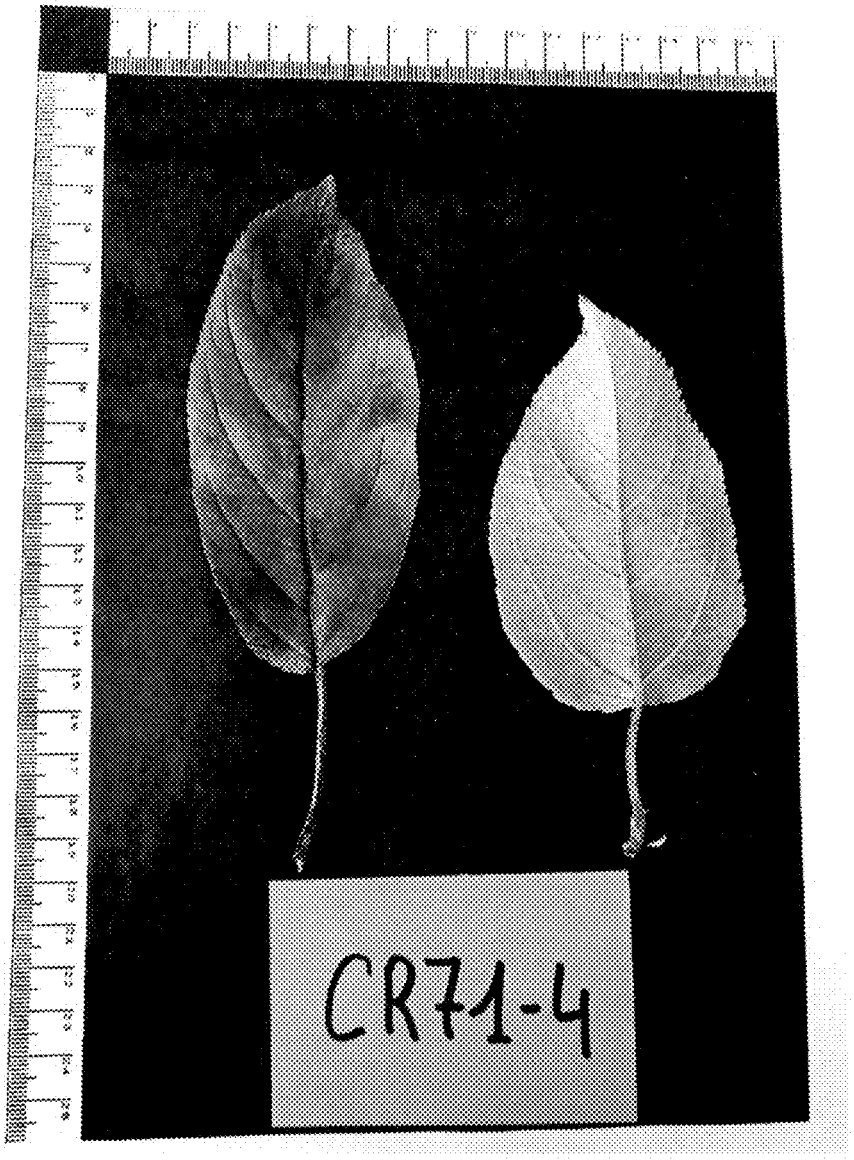
FIG. 4 is a photograph of leaves from an 'R205' apple tree.
Figure 5:
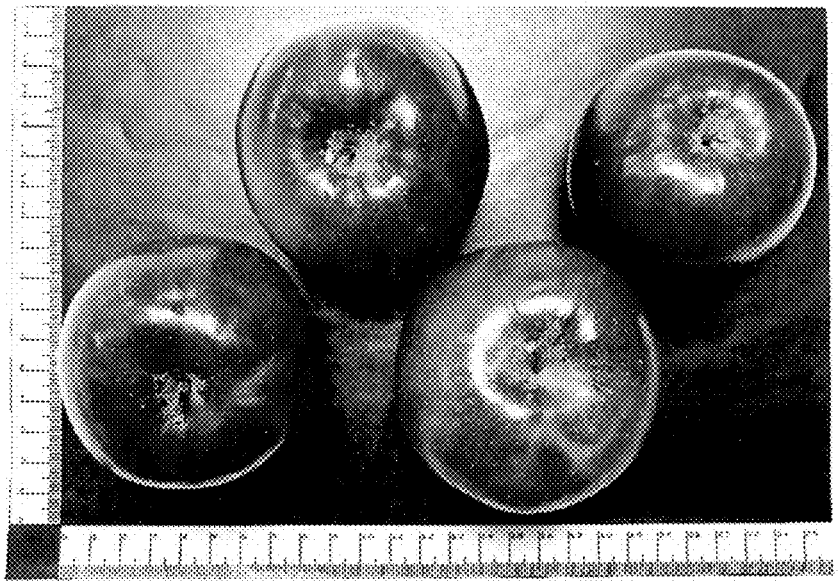
FIG. 5 is a photograph of a stem-end view of apples from an 'R205' apple tree.
Figure 6:
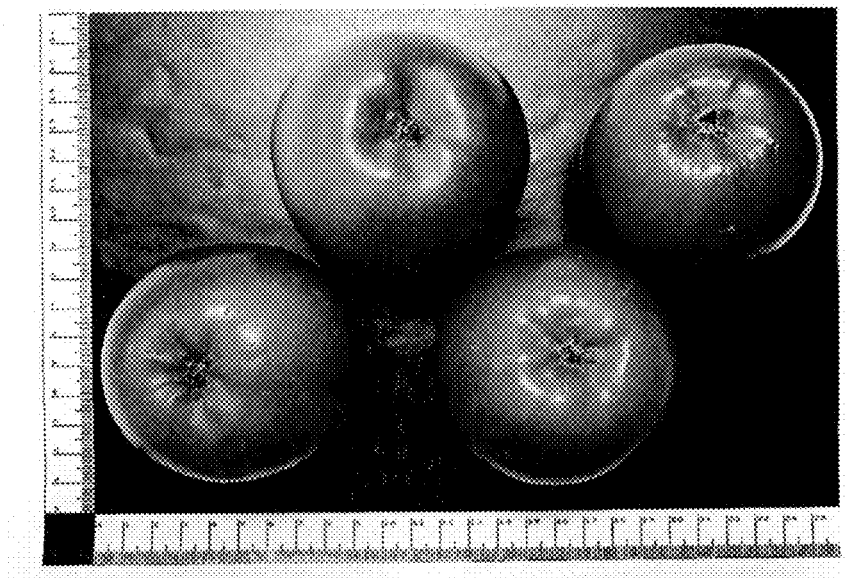
FIG. 6 is a photograph of a calyx-end view of apples from an 'R205' apple tree.
Figure 7:
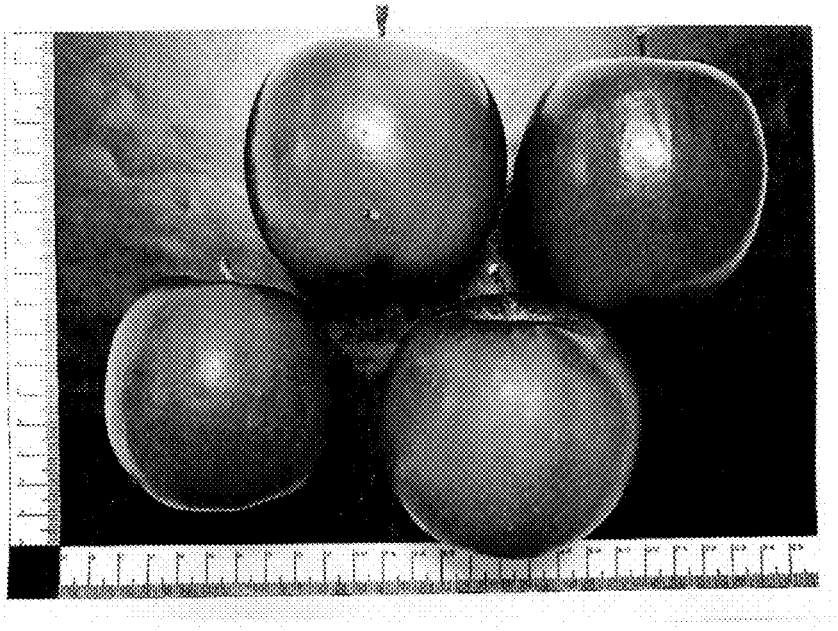
FIG. 7 is a photograph of a side view of apples from an 'R205' apple tree.
Figure 8:
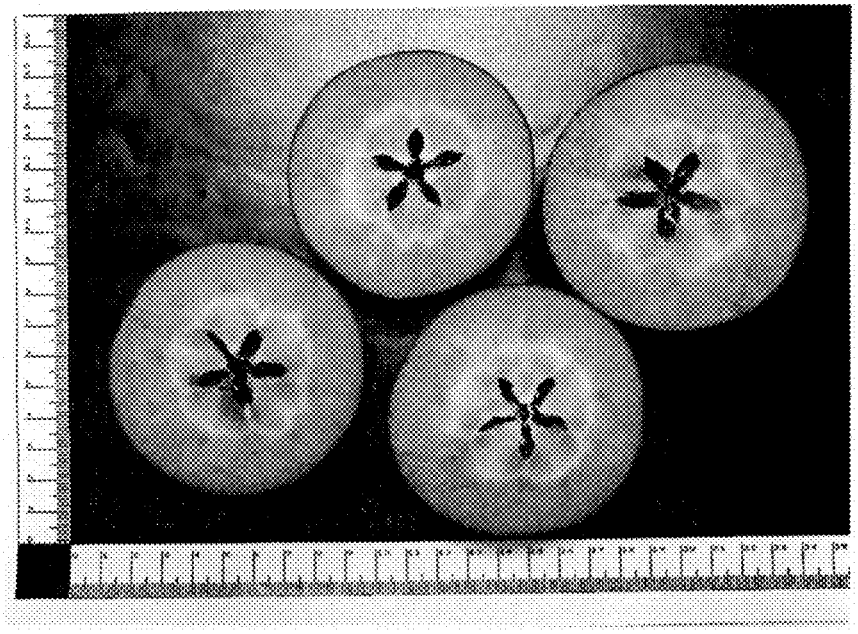
FIG. 8 is a photograph of sectioned apples from an 'R205' apple tree.
Figure 9:
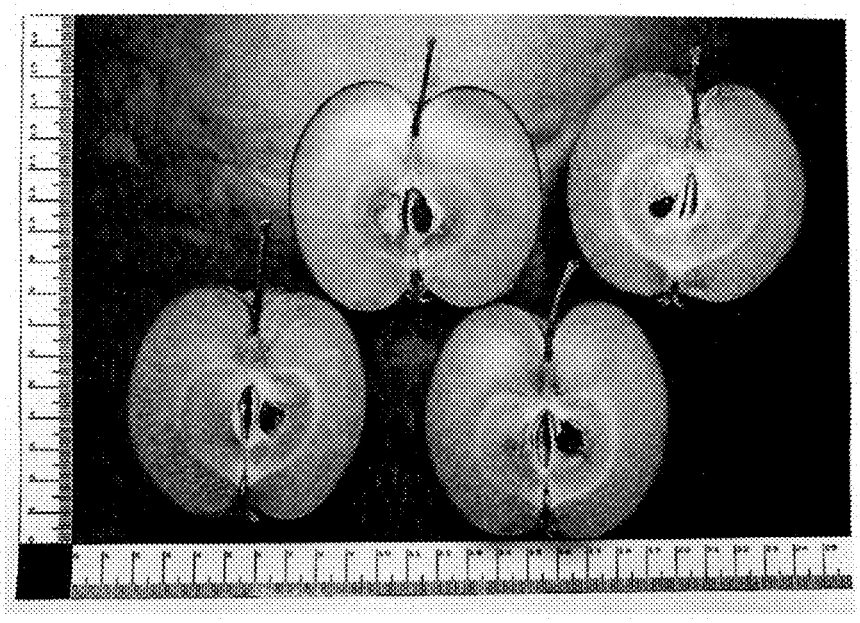
FIG. 9 is a photograph of sectioned apples from an 'R205' apple tree.

The following detailed botanical description was recorded at Seiches-sur-le-Loir, France during the 2020 and 2021 growing seasons. Descriptions of the tree, blossoms and leaves were recorded from trees planted in 2015 and grown on Pajam®2 'Cepiland' (U.S. Plant Pat. 7,715) rootstock. Described fruits were grown on trees planted in 2020 and grown on Pajam®2 'Cepiland' rootstock. All colors are described with reference to The Royal Horticultural Society Colour Chart ($6^{th}$ ed. 2015, reprinted 2019). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
- *Vigor*.—Medium.
- *Type*.—Ramified.
- *Habit*.—Spreading to drooping.
- *Bearing*.—On shoots.
- *Spread of mature tree*.—1.5 m after pruning.
- *Height*.—2.0 m after pruning.
- *Trunk diameter* (*at* 30 *cm above the graft*).—30 mm.
- *Bark texture*.—Rough.
- *Bark color*.—Greyed-purple N187D and greyed-orange 166A.
- *Lenticel length*.—2 mm.
- *Lenticel width*.—1 mm.
- *Lenticel shape*.—Oblong.
- *Lenticel color*.—Yellow-orange 20B.
- *Lenticel density*.—4 per $cm^2$.

Branch (fruiting branches located at about 1 m above the graft union):
- *Length*.—70 cm.
- *Diameter*.—12.5 mm.
- *Crotch angle*.—80°.
- *Bark color*.—Brown N200C and greyed-orange 166A.
- *Lenticel length*.—2 mm.
- *Lenticel width*.—1 mm.
- *Lenticel shape*.—Oblong.
- *Lenticel color*.—Yellow-orange 20B.
- *Lenticel density*.—6 per $cm^2$.

One year old shoot:
- *Length*.—35 cm.
- *Diameter*.—4.3 mm.
- *Color*.—Greyed-purple 187A.
- *Pubescence*.—Weak.
- *Internode length*.—28 mm.
- *Lenticel length*.—0.5 mm.
- *Lenticel width*.—0.5 mm.
- *Lenticel shape*.—Round.
- *Lenticel color*.—Yellow-orange 15D.
- *Lenticel density*.—12 per $cm^2$.
- *Color of vegetative buds*.—Greyed-purple 187A.
- *Shape of vegetative bud apex*.—Pointed.
- *Position of vegetative buds in relation to shoots*.—Adpressed.

Flower buds (described at balloon stage):
- *Quantity per spur*.—5.
- *Bud shape*.—Conical.
- *Apex shape*.—Rounded.
- *Length*.—10 mm.
- *Diameter*.—7 mm.
- *Color*.—Red-purple 58A.

Flowers:
- *Inflorescence type*.—Umbel.
- *Diameter of fully open flower*.—29 mm.
- *Depth of fully open flower*.—11 mm.
- *Relative position of petal margin*.—Free.
- *Number per cluster*.—Average 5.
- *Date of first bloom*.—April 7 (trees planted in 2020).
- *Date of full bloom*.—April 18 (trees planted in 2020).
- *Pollination requirement*.—Most varieties with similar bloom date.

Petals:
- *Number per flower*.—5.
- *Petal shape*.—Elliptic.
- *Length*.—16 mm.
- *Width*.—10 mm.
- *Apex shape*.—Rounded.
- *Base shape*.—Cuneate.
- *Margin*.—Entire.
- *Color of upper surface*.—Red-purple 71B.
- *Color of lower surface*.—Red-purple 70B.
- *Texture of upper surface*.—Smooth.
- *Texture of lower surface*.—Smooth.

Pistils:
- *Length*.—8 mm.
- *Color*.—Red 54D and greyed-yellow 160B.
- *Quantity per flower*.—5.

Stigma:
- *Diameter*.—0.5 mm.
- *Color*.—Greyed-yellow 160B.

Style:
- *Length*.—7 mm.
- *Color*.—Red 54D.

Ovary:
- *Length*.—4 mm.
- *Diameter*.—3 mm.
- *Color*.—Yellow-green 146C.

Anthers:
*Quantity.*—18 to 20.
*Position relative to stigma.*—Level to slightly above.
*Anther length.*—2 mm.
*Anther width.*—1 mm.
*Color of anther.*—Red-purple 70B.
*Pollen presence.*—Present in moderate quantity.
*Pollen color.*—Yellow-orange 15D.

Pedicel:
*Length.*—7 mm.
*Diameter.*—1 mm.
*Color.*—Greyed-green 194A.
*Pubescence.*—Strongly pubescent, white N155A.

Sepals:
*Quantity.*—5.
*Color of upper surface.*—Greyed-green 194A.
*Color of lower surface.*—Green 137C.
*Sepal shape.*—Triangular.
*Apex shape.*—Acute.
*Margin.*—Entire.
*Length.*—6 mm.
*Width.*—2 mm.
*Texture.*—Both surfaces canescent.
*Attitude in relation to corolla.*—Curved downward.

Leaves:
*Shape.*—Broad ovate.
*Length.*—100.3 mm.
*Width.*—57.7 mm.
*Length to width ratio.*—1.7.
*Blade margin.*—Serrulate.
*Apex.*—Acute with broad long acuminate tip.
*Base shape.*—Rounded.
*Texture.*—Upper surface — Glabrous.
*Texture.*—Lower surface — Canescent.
*Leaf color.*—Upper surface — Green 137A.
*Leaf color.*—Lower surface — Greyed-green 194A.
*Attitude in relation to shoot.*—Upwards.

Petiole:
*Length.*—41.1 mm.
*Diameter.*—2 mm.
*Color.*—Red-purple 59A.
*Color of anthocyanin at base.*—Purple N77A.

Stipules:
*Quantity.*—2 per leaf.
*Shape.*—Oblanceolate.
*Length.*—About 7 mm.
*Width.*—About 1 mm.
*Texture.*—Upper surface — Glabrous.
*Texture.*—Lower surface — Canescent.
*Color.*—Upper surface — Green 137A.
*Color.*—Lower surface — Greyed-green 194A.

Fruit:
*Quantity per cluster.*—3.
*Diameter.*—71.8 mm.
*Height.*—65 mm.
*Height to width ratio.*—0.9.
*Weight.*—167.1 g.
*General shape in profile.*—Cylindrical.
*Position of maximum diameter.*—At equator.
*Ribbing.*—Absent.
*Crowning at calyx end.*—Absent to weak.
*Bloom of skin.*—Absent to weak.
*Greasiness of skin.*—Absent to weak.
*Background color of skin.*—Yellow-orange 18B.
*Over color of skin.*—Greyed-purple 187A (dark red).
*Amount of over color.*—99%.
*Intensity of over color.*—Very intense.
*Pattern of over color.*—Only solid flush.
*Fruit lenticel color.*—Orange-white 159B.
*Fruit lenticel diameter.*—0.3 mm.
*Fruit lenticel shape.*—Round.
*Fruit lenticel density.*—Moderate.
*Russet around stalk cavity.*—Weak to medium; russet is rough.
*Russet on cheeks.*—Absent.
*Russet around eye basin.*—Absent.
*Length of stalk.*—25 mm.
*Diameter of stalk.*—1.66 mm.
*Stalk color.*—Greyed-purple 187A.
*Depth of stalk cavity.*—13.3 mm.
*Width of stalk cavity.*—30.3 mm.
*Depth of eye basin.*—2.3 mm.
*Width of eye basin.*—28.1 mm.
*Diameter of eye.*—4.2 mm.
*Aperture of eye.*—Closed.
*Length of sepal.*—5.1 mm.
*Firmness of flesh.*—Medium; 7.5 kg/cm$^3$ (2022 harvest).
*Flesh texture.*—Medium to coarse.
*Flesh color.*—Red N45C on 80% of flesh; white N155C on 20% of flesh.
*Number of locules.*—5.
*Aperture of locules.*—Mostly open.
*Locule length.*—10 mm.
*Locule width.*—5 mm.
*Flavor and aroma.*—Balanced with some astringency.
*Juiciness.*—Medium to high.
*Brix.*—12° Brix.

Seeds:
*Quantity per fruit.*—Average 7.5.
*Length.*—9.9 mm.
*Width.*—4.5 mm.
*Shape.*—Moderately elongated oval.
*Color.*—Brown 200B.

Harvest:
*Harvest date.*—Oct. 7, 2021; 10 days after 'Golden Delicious' (not patented).
*Number of picks.*—2.
*Productivity.*—About 8 kg per tree (3$^{rd}$ leaf trees grown on Pajam®2 'Cepiland' rootstock).

Disease resistance/susceptibility: None noted.
Storageability: Moderate; about 3 months at 3° C.
Market use: Fresh consumption.

The invention claimed is:

1. A new and distinct apple tree named 'R205' substantially as described and illustrated herein.

* * * * *